(12) United States Patent
Sen et al.

(10) Patent No.: US 11,077,045 B2
(45) Date of Patent: *Aug. 3, 2021

US011077045B2

(54) BLOOD MICROPERFUSION TO SKIN BY SHILAJIT

(71) Applicant: Natreon, Inc., New Brunswick, NJ (US)

(72) Inventors: Chandan K. Sen, Columbus, OH (US); Sanyasi R. Kalidindi, Monroe, NJ (US)

(73) Assignee: Natreon, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,876

(22) Filed: Jun. 26, 2018

(65) Prior Publication Data

US 2019/0388322 A1      Dec. 26, 2019

(51) Int. Cl.
*A61K 8/72* (2006.01)
*A61K 8/92* (2006.01)
*A61Q 19/08* (2006.01)
*A61K 8/49* (2006.01)

(52) U.S. Cl.
CPC .............. *A61K 8/498* (2013.01); *A61K 8/72* (2013.01); *A61K 8/92* (2013.01); *A61Q 19/08* (2013.01)

(58) Field of Classification Search
CPC . A61K 8/498; A61K 8/72; A61K 8/92; A61Q 19/08
USPC ........................................................ 514/455
See application file for complete search history.

(56) References Cited

U.S. PATENT DOCUMENTS

2005/0245434 A1* 11/2005 Ghosal ............... A61K 8/498
424/278.1
2016/0095881 A1    4/2016 Sen

OTHER PUBLICATIONS

NutraScience Labs (Can Shilajit be used to support skin health and healthy aging?, Jun. 9, 2016, https://www.nutrasciencelabs.com/blog/shilajit-linked-to-improved-collagen-synthesis-and-anti-aging) (Year: 2016).*
Micoperfusion is defined by Merriam-Webster (https://www.merriam-webster.com/medical/microperfusion,retrieved from the internet on Oct. 24, 2019). (Year: 2019).*
Bentov et al. (Microvasc Res., 100, Jul. 25-31, 2015) (Year: 2015).*
Xue, M., et al., Extracellular Matrix Reorganization During Wound Healing and Its Impact on Abnormal Scarring; Adv. Wound Care (New Rochelle) (2015) 4(3): p. 119-136).
Selfhacked. How to Fix a Leaky Blood Brain Barrier. Jul. 15, 2017; Retrieved from the Internet. Retrieved from [https://www.selfhacked.com/blog/fix-leaky-blood-brain-barrier/] p. 18 of 37; p. 26 of 37.
United States Patent and Trademark Office, "International Search Report" and "Written Opinion" dated Sep. 13, 2018 in PCT Application No. PCT/US2018/039593.

* cited by examiner

*Primary Examiner* — Yevgeny Valenrod
(74) *Attorney, Agent, or Firm* — Amin Talati Wasserman LLP; George M. Carrera, Jr.; Valerie Neymeyer-Tynkov

(57) ABSTRACT

Methods of using Shilajit or its individual components, or a combination of two or more of these components, to improve skin microperfusion, to upregulate ECM related genes in the skin, to increase endothelial cell migration and growth of blood vessels, and thus to improve skin health are presented herein.

9 Claims, 15 Drawing Sheets
(10 of 15 Drawing Sheet(s) Filed in Color)

BLOOD MICROPERFUSION TO SKIN BY SHILAJIT

TECHNICAL FIELD

The present invention relates to upregulating Extra Cellular Matrix (ECM) collagen genes and improving blood microperfusion to the skin and thus improving skin health through the use of Shilajit; its individual chemical constituents, including 3-hydroxy-dibenzo-α-pyrone, 3,8-dihydroxy-dibenzo-α-pyrone, dibenzo-α-pyrone chromoproteins, humic acid, fulvic acid, and more than forty (40) minerals; or combinations thereof.

BACKGROUND

Shilajit, also known as "Moomiyo," is found in the high altitudes of the Himalayan Mountains and is considered as one of the "wonder medicines" of Ayurveda, the traditional Indian system of medicine dating back to 3,500 B.C.E. Shilajit is regarded as one of the most important components in the Ayurvedic System of medicine and is also used as an adaptogen. S. Ghosal et al., "Shilajit I: chemical constituents," 65 J. PHARM. SCI. 772 (1976); C. Velmurugan et al., "Evaluation of safety profile of black shilajit after 91 days repeated administration in rats," 2 ASIAN PAC. J. TROP. BIOMED. 210 (2012). Shilajit is regarded as a "maharasa" (super-vitalizer) in Ayurveda. Shilajit is composed of rock humus, rock minerals, and organic substances that have been compressed by layers of rock mixed with marine organisms and microbial metabolites. Shilajit oozes out of the rocks in the Himalayas at higher altitudes ranging from 1,000 to 5,000 meters as black mass, as the rocks become warm during summer. C. Velmurugan et al., supra at 210. Shilajit contains fulvic acids ("FAs") as its main components, along with dibenzo-α-pyrones ("DBPs") and DBP chromoproteins, humic acid, and more than forty (40) minerals.

Shilajit is a resinous blackish-brown sticky tar-like herbo-mineral exudate that seeps from sedentary rocks of steep mountainous regions and has been considered as a panacea in Ayurvedic systems of medicine with a vast array of therapeutic properties (Agarwal, S. P., et al., "Shilajit: a review," *Phytother. Res.* (2007) 21(5): p. 401-5; Wilson, E., et al., "Review on shilajit used in traditional Indian medicine," *J. Ethnopharmacol.* (2011) 136(1): p. 1-9). Though geographic and environmental factors determine the composition of Shilajit (Agarwal, S. P., et al.), chemical characterization of Shilajit has revealed the presence of three major components. Dibenzo-α-pyrones (DBPs, also known as Urolithins) in free form as well as conjugated with chromoproteins, fulvic acid with DBP core nucleus and humic acid, the major component being fulvic acid (Wilson, E., et al.; S. G). Shilajit has had many applications in folk medicine with numerous anecdotal reports of therapeutic efficacy. Being used as a rejuvenator since ages past (Wilson, E., et al.), Shilajit and its active constituents have been reported to possess an array of pharmacological properties including adaptogenic, antioxidant, anti-inflammatory, immunomodulatory, anti-diabetic and neurological properties (Stohs, S. J., "Safety and efficacy of shilajit (mumie, moomiyo)," *Phytother. Res.* (2014) 28(4): p. 475-9).

The skin comprises of one sixth of the human body and serves as a protective barrier between the internal organs of the body and the external environment (Farage, M. A., et al., "Characteristics of the Aging Skin," *Adv. Wound Care* (New Rochelle), (2013) 2(1): p. 5-10). Apart from its protective role, the skin aids in maintenance of body temperature and internal hydration, sensory functions, and immunological surveillance (Farage, M. A., et al.). However, in-spite of being extremely resilient, like all other systems, the skin eventually yields to the inevitable effects of aging. Skin aging is characterized by wrinkles, dryness, laxity, thinning, irregular pigmentation, and loss of elasticity (Konno, M., et al., "Adipose-derived mesenchymal stem cells and regenerative medicine," *Dev. Growth Differ.* (2013) 55(3): p. 309-18). Decrease in dermal thickness and vascularity is a hallmark of cutaneous aging (Amirkhani, M. A., et al., "Rejuvenation of facial skin and improvement in the dermal architecture by transplantation of autologous stromal vascular fraction: a clinical study," *Bioimpacts* (2016) 6(3): p. 149-154). Increased age is associated with decreased cutaneous perfusion (Waller, J. M. and H. I. Maibach, "Age and skin structure and function, a quantitative approach (I): blood flow, pH, thickness, and ultrasound echogenicity," *Skin Res. Technol.* (2005) 11(4): p. 221-35).

Optimal circulation is a pre-requisite for proper metabolism and functioning of the human body. Skin blood perfusion and oxygenation depends upon cardiovascular, hormonal and circulatory health in humans and provides sociosexual signals of underlying physiology, dominance and reproductive status (Stephen, I. D., et al., "Skin blood perfusion and oxygenation colour affect perceived human health," *PLoS One* (2009) 4(4): p. e5083). Blood flow in the skin has major thermoregulatory function, nutritional role and wound healing effects (Kobayashi, H. and H. Tagami, "Distinct locational differences observable in biophysical functions of the facial skin: with special emphasis on the poor functional properties of the stratum corneum of the perioral region," *Int. J. Cosmet. Sci.* 2004. 26(2): p. 91-101). Decreased blood flow leads to inflammation and decelerates wound healing responses (Chen, Y. and J. Lyga, "Brain-skin connection: stress, inflammation and skin aging," *Inflamm. Allergy Drug Targets* (2014) 13(3): p. 177-90). In addition, inadequate circulation in the skin leads to cosmetic defects like unattractive skin tone and skin discoloration. Exposure to extreme temperatures induces cutaneous vasoconstriction and vasodilation via distinct sympathetic reflex and locally mediated pathways which are impaired with aging (Holowatz, L. A., C. Thompson-Torgerson, and W. L. Kenney, "Aging and the control of human skin blood flow," *Front Biosci.* (Landmark Ed.), (2010) 15: p. 718-39). Decrease in dermal vascularity is commonly encountered during cutaneous aging (Amirkhani, M. A., et al.). Increased age is associated with decreased cutaneous perfusion which in turn will adversely affect aging (Waller, J. M. and H. I. Maibach). In addition, aging skin has negative psychological effects in women. Chemical compounds present in anti-aging creams and cosmetics are a major threat, paving way to the use of natural products. However, literature on role of nutraceuticals and natural products on skin vasculature and microperfusion is scanty. Low-dose L-arginine administration was found to increase microperfusion of rat skin (Ohta, F., et al., "Low-dose L-arginine administration increases microperfusion of hindlimb muscle without affecting blood pressure in rats," *Proc. Natl. Acad. Sci. USA* (2007) 104(4): p. 1407-11). Blood flow was improved in feet of subjects with diabetes with use of a transdermal preparation of L-arginine (Fossel, E. T., "Improvement of temperature and flow in feet of subjects with diabetes with use of a transdermal preparation of L-arginine: a pilot study," *Diabetes Care* (2004) 27(1): p. 284-5).

Dietary supplements, comprising some of the most valuable and safe substances, not only prevent and treat serious chronic and acute diseases associated with mortality, but also help combat health problems that cause discomfort and disability. Similar to their role in prevention and treatment of diseases, evidence suggests that dietary supplements provide protection from accelerated aging that result from oxygen free-radical damage, inflammation, and glycation (Janson, M.), inter alia. The present study was aimed at determining the effect of Shilajit supplementation on skin rejuvenation.

A recent human clinical study provided evidence that oral supplementation of a purified and standardized Shilajit extract significantly upregulated Extra Cellular Matrix (ECM)-related genes, especially genes encoding several collagens, in the skeletal muscle of obese (BMI 25-35) individuals, and such effect was highly synergistic with exercise (US 2016/0095881 A1). Based on these results, it was hypothesized that Shilajit may improve skin health.

The extracellular matrix (ECM) provides structural, organizational, and orientation to cells and tissues and controls cellular functions (Xue, M. and C. J. Jackson, "Extracellular Matrix Reorganization During Wound Healing and Its Impact on Abnormal Scarring," *Adv. Wound Care* (New Rochelle), (2015) 4(3): p. 119-136). Collagens constitute the major component of ECM and provide structural support to resident cells.

Collagen is the body's major structural protein composed of three protein chains wound together in a tight triple helix. This unique structure gives collagen a greater tensile strength than steel. Approximately thirty-three (33) percent of the protein in the human body is collagen. Collagen, in the form of elongated fibrils, is mostly found in fibrous tissues such as tendons, ligaments, and skin.

Types of Collagen:

Collagen occurs in many places throughout the body. Over ninety (90) percent of the collagen in the body is type I. So far, twenty-eight (28) types of collagen have been identified and described. The five (5) most common types are:

Collagen I: skin, tendon, vascular ligature, organs, bone (main component of the organic part of bone);
Collagen II: cartilage (main component of cartilage);
Collagen III: reticulate (main component of reticular fibers), commonly found alongside Collagen I;
Collagen IV: forms basal lamina, the epithelium-secreted layer of the basement membrane; and
Collagen V: cell surfaces, hair, and placenta.

Collagen is important to health because it plays a key role in maintaining the health of skin as detailed below.

Skin Health

Collagen plays an important role in skin health. Collagen I and Collagen III are formed in human skin in a higher proportion relative to other types of collagen and are maintained in a fixed proportion relative to one another in normal skin tissue. Collagen I constitutes about seventy (70) percent of collagen in the skin, with Collagen III constituting about ten (10) percent of collagen in the skin and Collagens IV, V, VI, and VII each constituting trace amounts of collagen in the skin. Collagen maintains firmness and elasticity of the skin. Collagen, in the form of collagen hydrolysate, keeps skin hydrated. Decreases in the amount of collagen in the body with age result in sag, lines, wrinkles, lack of tension and elasticity, and delay in wound healing processes.

Degradation and Decreased Production of Collagen

With age, collagen degrades, and there is a decrease in the production of collagen. As a result, fine lines and wrinkles appear in the skin. Skin also loses its elasticity and sags. Collagen can be preserved by reducing degradation of existing collagen and increasing the production of new collagen. Some commonly used methods to reduce degradation of skin collagen are: (a) protecting the skin from UVA and UVB rays; (b) avoiding excessive exposure to sunlight; (c) having a diet including antioxidants to fight free radicals; (d) ingesting Vitamin C, which accelerates production of new collagen; (e) supplementing with collagen-stimulating peptides; and (f) increasing the intrinsic ability of the body to produce new collagen.

Several animals and human studies (Das, A., et al., "The Human Skeletal Muscle Transcriptome in Response to Oral Shilajit Supplementation," *J. Med. Food* (2016) 19(7): p. 701-9; Biswas, T. K., et al., "Clinical evaluation of spermatogenic activity of processed Shilajit in oligospermia," *Andrologia* (2010) 42(1): p. 48-56; Sharma, P., et al., "Shilajit: evaluation of its effects on blood chemistry of normal human subjects," *Anc. Sci. Life* (2003) 23(2): p. 114-9) have demonstrated the safety of Shilajit leading to its GRAS (Generally Recognized As Safe) status in 2015 (Stohs, S. J., 2014). However, no studies were conducted to find the effect of Shilajit on human skin.

SUMMARY OF THE INVENTION

The clinical studies of effects of oral supplementation of Shilajit on skin health indicate that orally administered Shilajit can upregulate ECM collagen gene. Furthermore, Shilajit surprisingly improved blood microperfusion to the skin, which is supported by endothelial cell migration and growth of blood vessels, as identified by Ingenuity Pathway Analysis. This is a significant finding, as the blood flow to the skin decreases with aging, and any improvement in blood flow to the skin may contribute to anti-aging of the skin. As a result, present invention demonstrates that oral supplementation of Shilajit can improve skin health.

The present invention relates to an oral dosage form of Shilajit and method of administering said dosage form to a human subject to upregulate the ECM genes, such as Col1A1, Col5A2 and Col14A1. The clinical results indicate that upregulation of the ECM genes, such as Col1A1, Col5A2 and Col14A1, was statistically significant ($p \leq 0.05$) at 125 mg b.i.d. dose of Shilajit, when compared to placebo. In spite of the various claims and studies of the rejuvenating properties of Shilajit, the mechanism remains unclear. The present invention, for the first time, identifies a mechanism of action of Shilajit on skin rejuvenation.

The present invention relates to a method of increasing skin microperfusion through administration of oral supplementation of PrimaVie® Shilajit (PVS) formulation, e.g. capsules. GeneChip® analysis followed by IPA analysis and RTPCR confirmed that the improved microvasculature was concomitant to the increased genes related to endothelial cell migration and growth of blood vessels.

In an embodiment, PrimaVie® Shilajit (PVS) formulation not only upregulates the angiogenic genes in the skin but also rejuvenates the skin via upregulation of ECM related genes and new collagen formation.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 depicts, in one embodiment of present invention, that PrimaVie improves skin microperfusion. FIG. 1C, 3D Scatterplot of the Visible Bands of Matlab processed dermascopic images;

FIG. 2 depicts, in one embodiment of present invention, heat map illustrating cluster of transcripts that were sensitive to PVS supplementation. PVS-sensitive transcripts were subjected to hierarchical clustering.

DETAILED DESCRIPTION

Figure 1A:
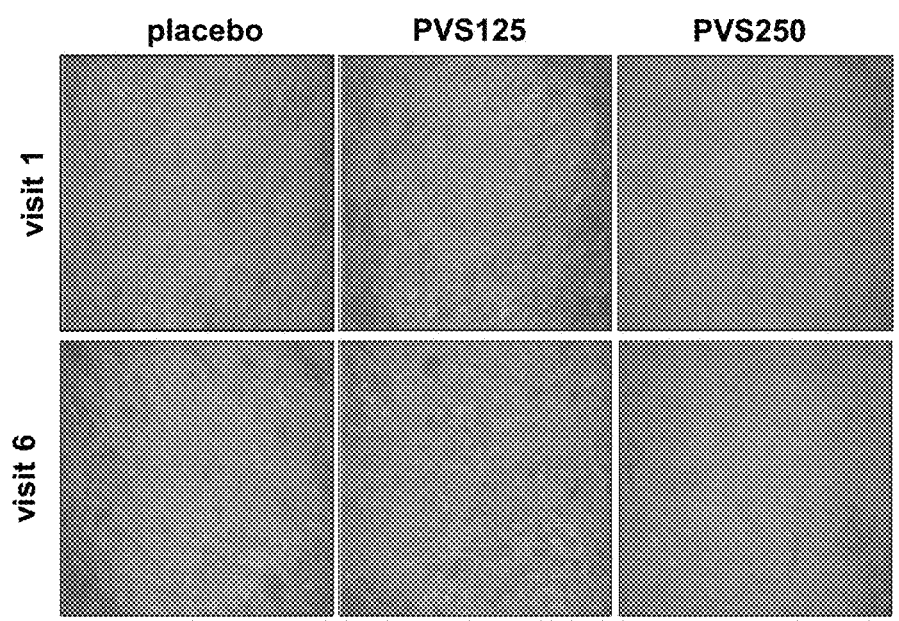
FIG. 1A, Dermascopic images of the cheek.

In one embodiment of the present invention, a method of using oral supplementation of PVS to increase skin microperfusion is provided. The method comprises administering a dose of Shilajit between about 20 milligrams and about 2,000 milligrams per day to a human subject. The embodiment provides that PVS supplementation improves skin microperfusion.

In another embodiment of the present invention, a method of using oral supplementation of PVS to improve microvasculature is provided. The method comprises administering a dose of Shilajit between about 20 milligrams and about 2,000 milligrams per day to a human subject. An unbiased screening of the skin transcriptome, GeneChip® analysis followed by IPA analysis, and RTPCR were performed after PVS supplementation. The clinical study confirmed that the improved microvasculature was concomitant to the increased genes related to endothelial cell migration and growth of blood vessels. The embodiment provides that oral Shilajit supplementation in human upregulates genes related to endothelial cell migration and growth of blood vessels, resulting in improved skin microperfusion.

In another embodiment of the present invention, a method of using PVS to upregulate the angiogenic genes in the skin and rejuvenate the skin via upregulation of ECM related genes and new collagen formation is provided.

In order to determine the effect of Shilajit on the skin of a human, a human clinical study was conducted. The study was aimed at determining the effect of Shilajit supplementation on skin health of human subjects. The hypothesis of the clinical study was that oral supplementation of Shilajit would influence ECM-associated gene expression in human skin.

Study Subjects and Experimental Design

Thus, a human clinical study was performed to evaluate the effects of oral supplementation of Shilajit on skin health. The institutional review board (IRB) of The Ohio State University approved the study protocols (clinicaltrials.gov NCT02762032) and materials. All subjects provided written informed consent before participation in the study. Female subjects between the ages of 30 to 65 were included in the study. Three groups (each with n=15) of subjects were formed with randomization software. Control group-1 received placebo capsules (Microcrystalline cellulose, NF—96%, Silicon dioxide, Fumed, NF—1.0%, Croscarmellose sodium, NF—2.0%, Magnesium Stearate, NF—1.0%) and group-2 and group-3 received 125 mg or 250 mg capsules of PVS b.i.d., respectively. Oral supplementation was continued for 14 weeks and six assessment visits were performed during this duration of study. The experimental study design consisted of six study visits during the 14-week study period: visit 1: baseline visit; visit 2: after 2 weeks of oral supplement of PVS; visit 3: after 4 weeks of oral supplement of PVS; visit 4: after 8 weeks of oral supplement of PVS; visit 5: after 12 weeks of oral supplement of PVS; visit 6: after 14 weeks of oral supplement of PVS. Each subject received 125 mg, 250 mg of PVS (Natreon, Inc., New Brunswick, N.J., USA) or placebo capsules twice a day for the entire study. Supplement randomization, based on one of the three arms, was done at study visit 1, and distribution of the study product was done at each study visit. During each visit imaging and skin assessment was performed. During the course of the study, the medical and dietary history and medications were recorded, photography of the face (left, right and front) was done, non-invasive assessments including Trans-epidermal Water Loss, hydration, elasticity, laser speckle perfusion, a skin biopsy of left inner upper arm (only at study visits 2 and 6), adverse event review, and supplement count/compliance review were done. Any self-reported deviations in diet were recorded. The subjects were excluded from the study if any one of the following medications was used for management/ treatment of CVD-related disorders: steroids (e.g., Prednisone etc.), beta-blockers, hydrochlorothiazide, statins (e.g., Crestor, Lipitor, etc.), aspirin, or ACE inhibitors. Pregnant females as well as individuals who were therapeutically immunocompromised were also excluded from the study. The demographics of subjects participating in this study are presented in Table 1.

TABLE 1

Patient Demographics

| Parameters | Values |
|---|---|
| Subjects (No.) | 45 |
| Ages (years) | 42 ± 7.9 |
| Body Weight (kg) | 76.2 ± 18.4 |
| Body Mass Index (kg · m$^{-2}$) | 29.5 ± 9.2 |
| Race | |
| Caucasian | 38 |
| African American | 6 |
| Asian | 1 |

Materials and Methods:

PrimaVie®, described in U.S. Pat. Nos. 6,869,612, and 6,558,712, herein incorporated by reference, is a purified and standardized Shilajit extract for nutraceutical use. Research indicates that PrimaVie® Shilajit is standardized to have not less than 60% fulvic acid and equivalents with high levels of dibenzo-α-pyrones and dibenzo-α-pyrone chromoproteins (Ghosal, S., J. P. Reddy, and V. K. Lal, "Shilajit I: chemical constituents," *J. Pharm. Sci.* (1976) 65(5): p. 772-3; Meena, H., et al., "Shilajit: A panacea for high-altitude problems," *Int. J. Ayurveda Res.* (2010) 1(1): p. 37-40). The test product, PrimaVie® Shilajit (PVS) Capsules, 125 mg, 250 mg and placebo were supplied by Natreon, Inc., 2D Janine Place, New Brunswick, N.J. 08901. The capsules contained standard components including gelatin, microcrystalline cellulose, croscarmellose sodium, fumed silicon-dioxide and magnesium stearate as excipients, which are of NF grade.

The clinical study may be further understood in connection with the following Examples and embodiments. In addition, the following non-limiting Examples and embodiments are provided to illustrate the invention.

Example 1

Dermascopic Image Processing of Skin Microperfusion

A MatLab (Mathworks Inc., Natick, Mass.) program code was written locally. Images from Dermascopic imaging system were transferred to Joint Photographic Experts Group (JPEG) image format. The JPEG images were processed to get multi-color images which were used for the detection of cell density and granulated tissue in normal skin. Equal area regions of interest (ROIs) were traced around the wound site and signal intensity was computed. Two dimensional (2D) 'trapz( )' MatLab function algorithm was used to calculate the area under the curve (AUC) by integrating intensity units over area of interest, which is a measure of total energy over the ROI.

Figure 1B:
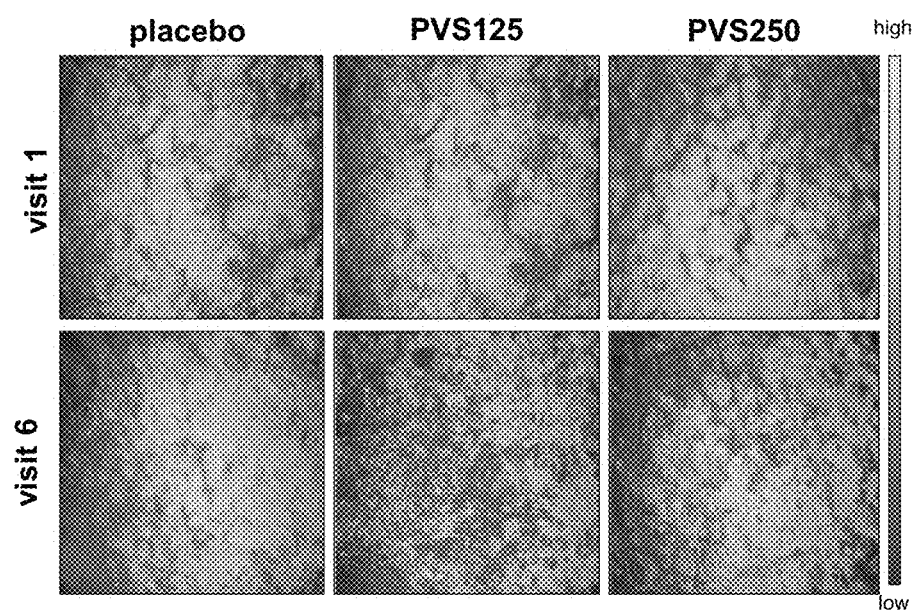
FIG. 1B, Matlab multicolor processed dermascopic images.
Figure 1C:
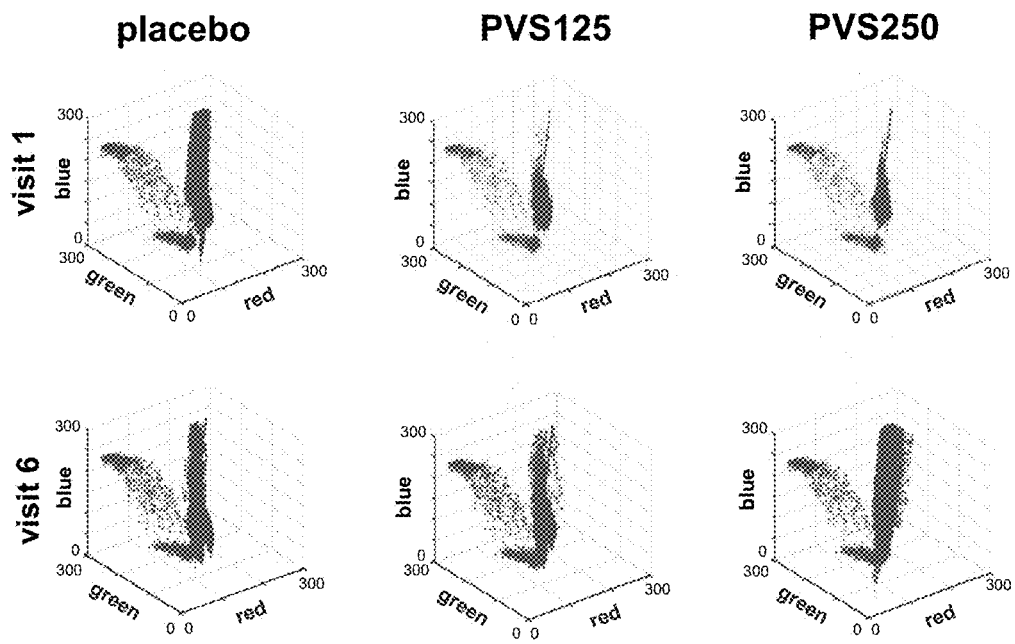
Figure 1D:
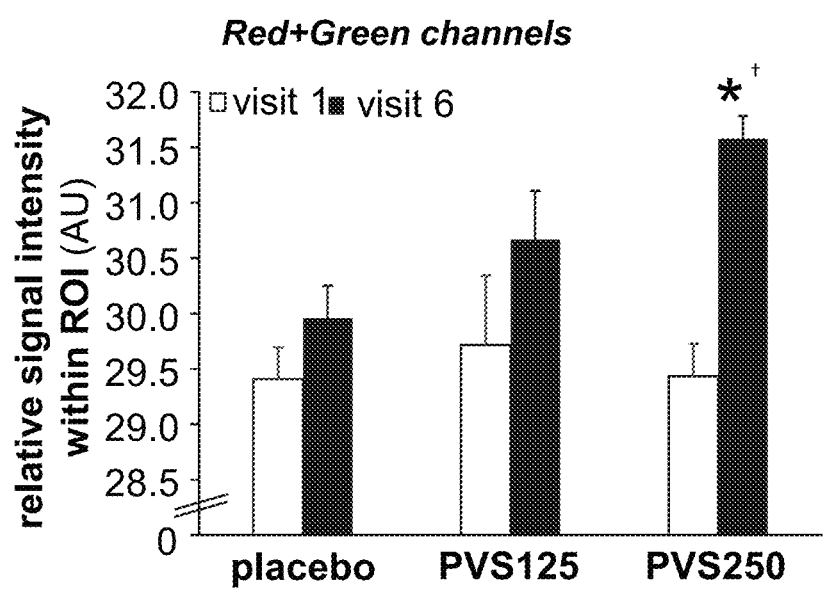
FIG. 1D, The sum of the area under the curve of red and green channels were plotted graphically. The intensity of the red and green channels were calculated from the multicolor images processed by Matlab software from the raw dermascopic images. Data are mean±SEM (n=13); *$p<0.05$ compared to the baseline visit. †$p<0.05$ compared to placebo.

Dermascopic images were used to determine if PVS supplementation had any effect on skin microperfusion. Increased reddish hue indicative of improved perfusion image was enhanced when processed using MatLab software. Increased skin coloration with oral supplementation of Shilajit was statistically significant at 250 mg dose, but not at 125 mg dose, compared to the placebo (See, FIGS. 1A and 1B).

Example 2

Transcriptome Profiling of Skin Following Oral PVS Supplementation a. Skin Biopsy Collection Biopsy site: Left inner arm. Biopsy specimens were taken with a 3 mm punch from the upper inner left arm at week 2 and week 14. Wound care materials and care instructions were provided to the subjects. Biopsy specimens were processed for mRNA expression profiling and RT-PCR.

b. GeneChip Probe Array Analyses

GeneChip® probe array analysis was performed using Affymetrix Clariom™ D Assay as described previously (Roy, S., et al., "Characterization of the acute temporal changes in excisional murine cutaneous wound inflammation by screening of the wound-edge transcriptome," *Physiol. Genomics* (2008) 34(2): p. 162-84; Roy, S., et al., "Transcriptome-wide analysis of blood vessels laser captured from human skin and chronic wound-edge tissue," *Proc. Natl. Acad. Sci. USA* (2007) 104(36): p. 14472-7; Das, A., et al., "The Human Skeletal Muscle Transcriptome in Response to Oral Shilajit Supplementation," *J. Med. Food* (2016) 19(7): p. 701-9) to identify sets of genes differentially expressed in the skin samples of different time periods. Briefly, total RNA was isolated using the miRVana Isolation Kit according to the manufacturer's protocol (Thermo Fisher Scientific, Waltham, Mass., USA). RNA integrity was evaluated using the Agilent 2100 Bioanalyzer (Agilent, Santa Clara, Calif., USA). The isolated RNA was used to generate ss-c-DNA according to the manufacturer's protocol in the GeneChip® WT PLUS Reagent Kit Biotin-labeled Reagent Kit. Biotin-labeled ss-cDNA was hybridized, washed, and stained on the Affymetrix Fluidics Station 450 according to the manufacturer's protocol and scanned with the Affymetrix GeneChip Scanner 3000 7G (Affymetrix, Santa Clara, Calif.) in our own facilities as described earlier (Roy, S., et al. 2008; Roy, S., et al. 2007; Das, A., et al.). The expression data have been submitted to the Gene Expression Omnibus (GEO) at NCBI (http://www.ncbi.nlm.nih.gov/geo/) with the series accession number GSE114170. GCOS (Gene Chip Operating Software, Affymetrix) was employed for data acquisition and image processing. Raw data were analyzed using Genespring GX (Agilent, Santa Clara Calif.). Additional processing of data was performed using dChip software (Harvard University) (Roy, S., et al. 2008; Roy, S., et al. 2007; Das, A., et al.). GC-RMA (Gene Spring GX, Agilent, Santa Clara Calif.) was applied for data normalization. Differentially expressed genes were identified using a two-class t-test where significance level was set at p<0.05 with Benjamin-Hochberg correction for false discovery rate (Das, A., et al.; Roy, S., et al., "Characterization of a preclinical model of chronic ischemic wound," *Physiol. Genomics* (2009) 37(3): p. 211-24). The genes that were significantly upregulated were subjected to functional analysis using DAVID (Database for Annotation, Visualization and Integrated Discovery NIAID, NIH) and gene ontology (GO).

c. Statistical Analysis

Student's t test was used to determine significant differences across baseline/visit 2 and final visit. In case of RTPCR, since fold change values used in the analyses were not normal, the values were transformed using natural logarithm, and then use the transformed values for all the subsequent analyses that follow. For RTPCR, treatment comparisons among multiple groups were tested using multivariate analysis of variance (MANOVA) on fold changes of all genes to compare if the fold change values for all the gene expressions are jointly different in the treatment groups compared to the placebo. p<0.05 was considered statistically significant.

d. Transcriptome Profiling of Skin Following Oral PVS Supplementation

Figure 2A:
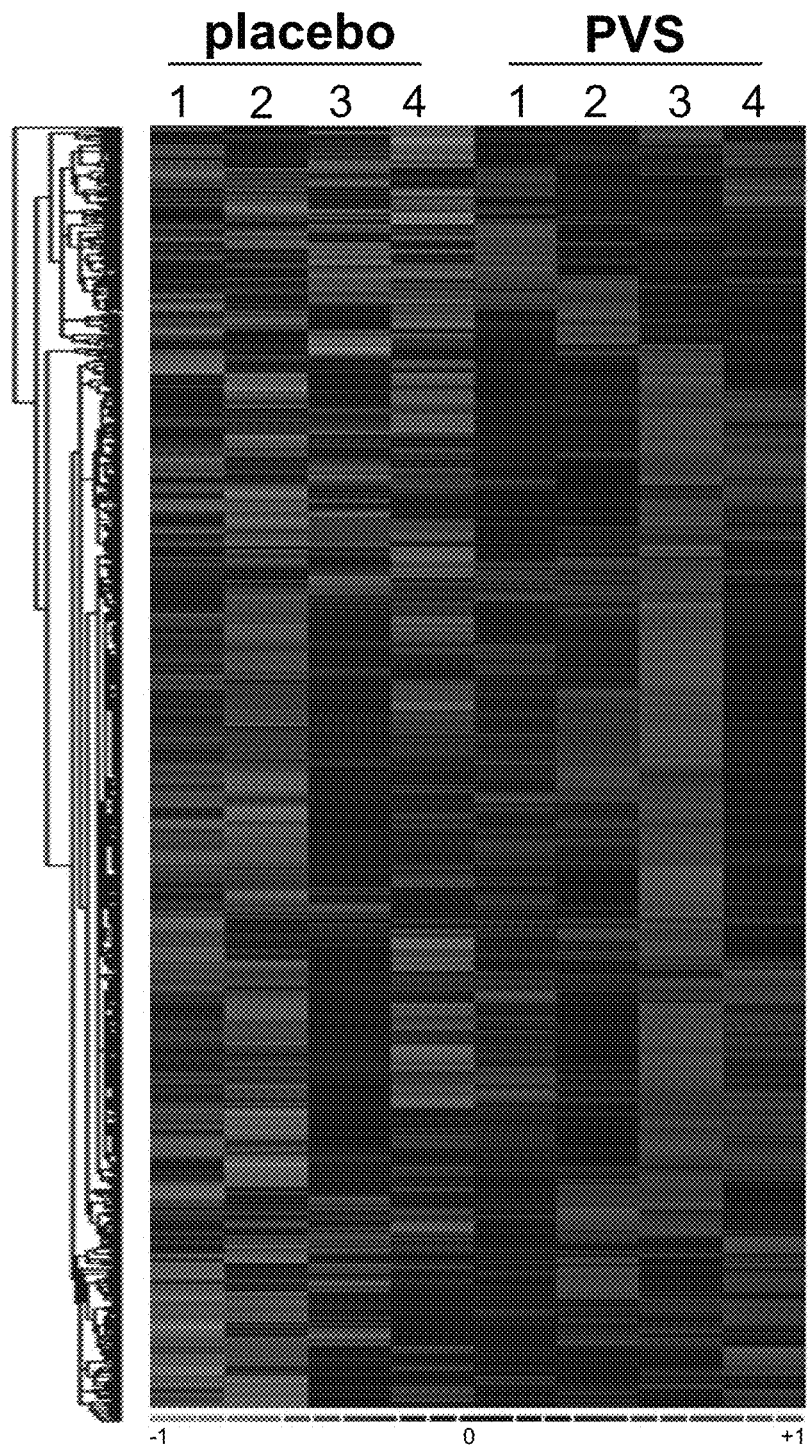
FIG. 2A, heat map illustrating cluster of transcripts that were sensitive to PVS supplementation.
Figure 2B:
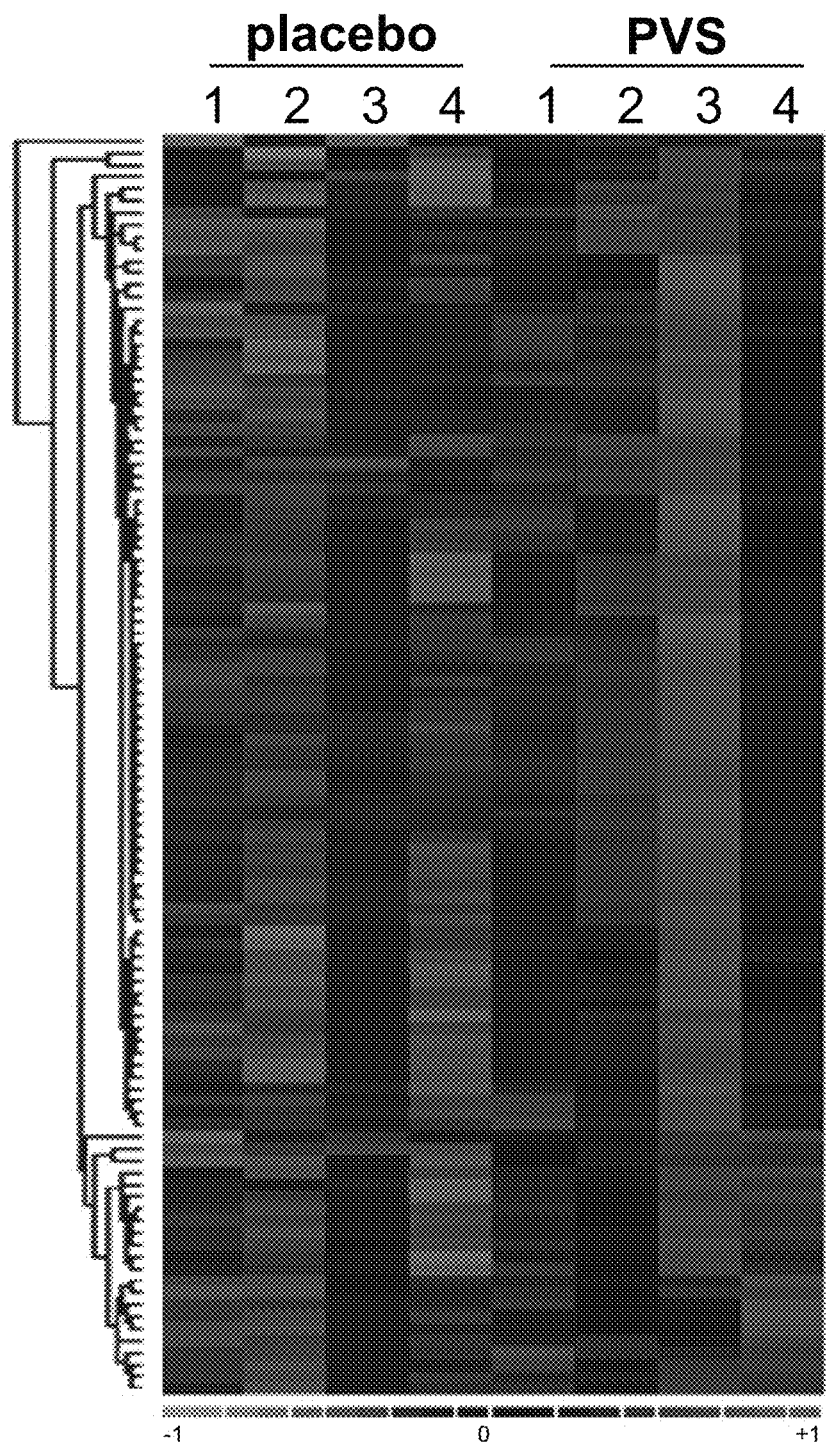
FIG. 2B, heat map (top 100 candidates) illustrating cluster of transcripts that were sensitive to PVS supplementation.

Skin samples were collected at visit 2 and visit 6. RNA extraction and target labeling were done, and GeneChip® data analysis was performed from skin samples collected on visit 6, using Affymetrix Clariom™ D Assay as described previously (Roy, S., et al. 2008; Roy, S., et al. 2007) to determine the changes in the transcriptomes of skin in response to oral PVS supplementation. The high-resolution array design contains an >6.0 million probes covering coding transcripts and non-coding transcripts. About 70% of the probes on this array cover exons for coding transcripts, and the remaining 30% of probes on the array cover exon-exon splice junctions and non-coding transcripts (Affymetrix. http://www.affymetrix.com/catalog/prod760002/AFFY/Human-Transcriptome-Array-2.0#1_1, accesses on Aug. 9, 2015. [cited 2015 Aug. 9]). See, FIGS. 2A and 2B.

Example 3

Upregulation of ECM Related Genes Induced by PVS Supplementation a. Validation of Microarray Results Using Quantitative Real-Time PCR For gene expression studies, total cDNA synthesis was achieved by using the SuperScript III First Strand Synthesis System (Thermo Fisher Scientific). Selected differentially-expressed candidate genes were verified by real-time PCR by using SYBR green-I and primers as previously described (Das, A., et al.; Roy, S., et al., "Characterization of perceived hyperoxia in isolated primary cardiac fibroblasts and in the reoxygenated heart," *J. Biol. Chem.* (2003) 278(47): p. 47129-35; Roy, S., et al., "Wound site neutrophil transcriptome in response to psychological stress in young men," *Gene Expr.* (2005) 12(4-6): p. 273-87). β-actin was used as a reference housekeeping gene.

Skin biopsy procedures and methods of statistical analysis for RT-PCR are disclosed in Example 2.

b. Pathway Analysis and Validation Using RT-PCR

Figure 3A:
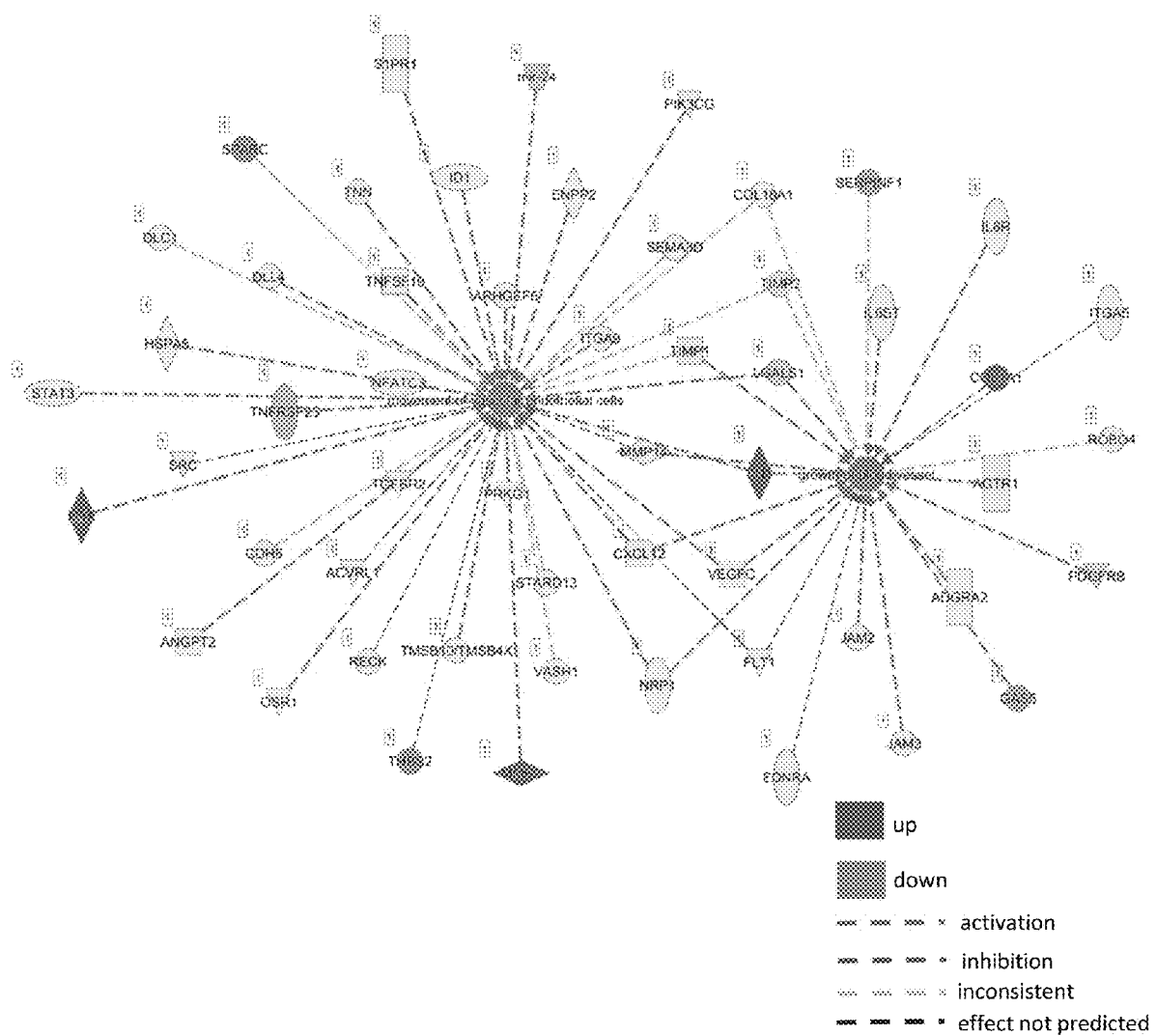
FIGS. 3A, 3B, and 3C depict, in an embodiment of present invention, ingenuity pathway analysis (IPA) showing that the supplementation of PVS increases genes involved in the movement of endothelial cells and growth of blood vessels (FIG. 3A), and further through the VEGFA (FIG. 3B) and TGFβ1 (FIG. 3C) pathways, respectively. (Up/Down in FIG. 3A stand for up/down regulation of the genes).
Figure 3B:
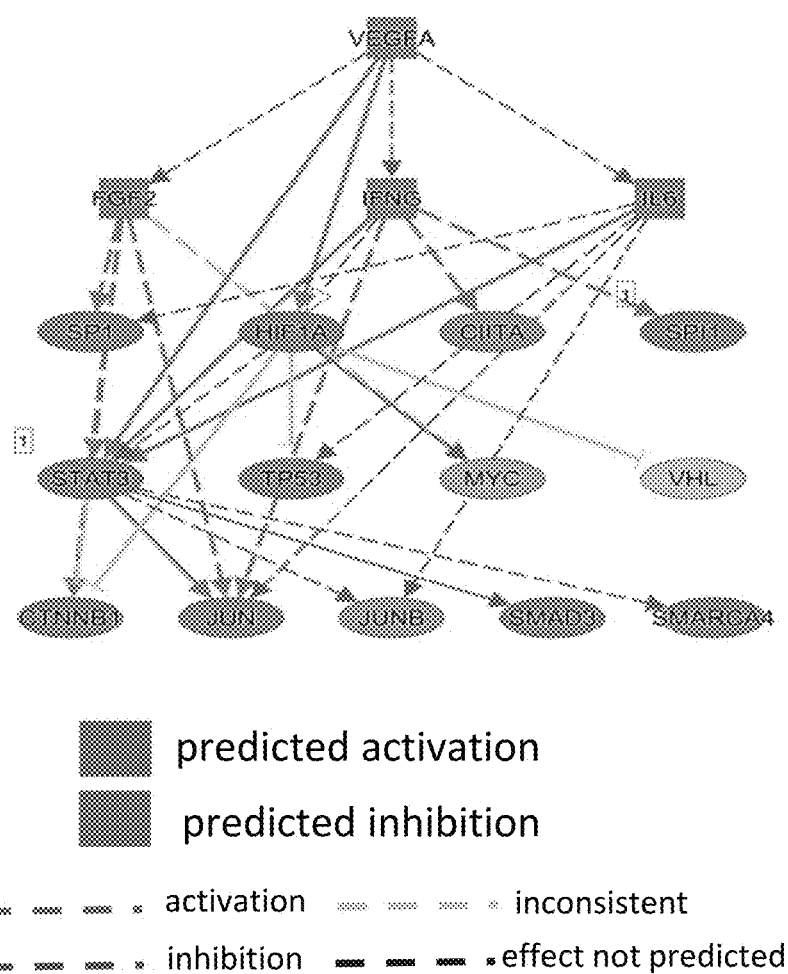
Figure 3C:
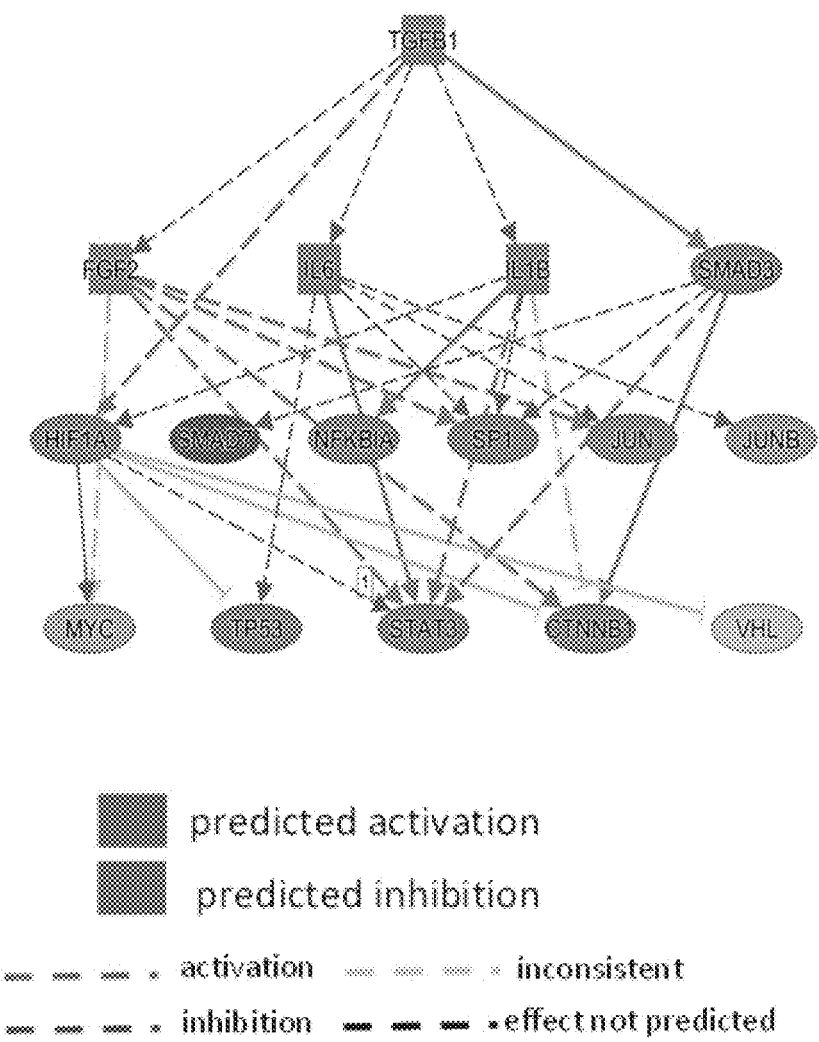
Figure 4:
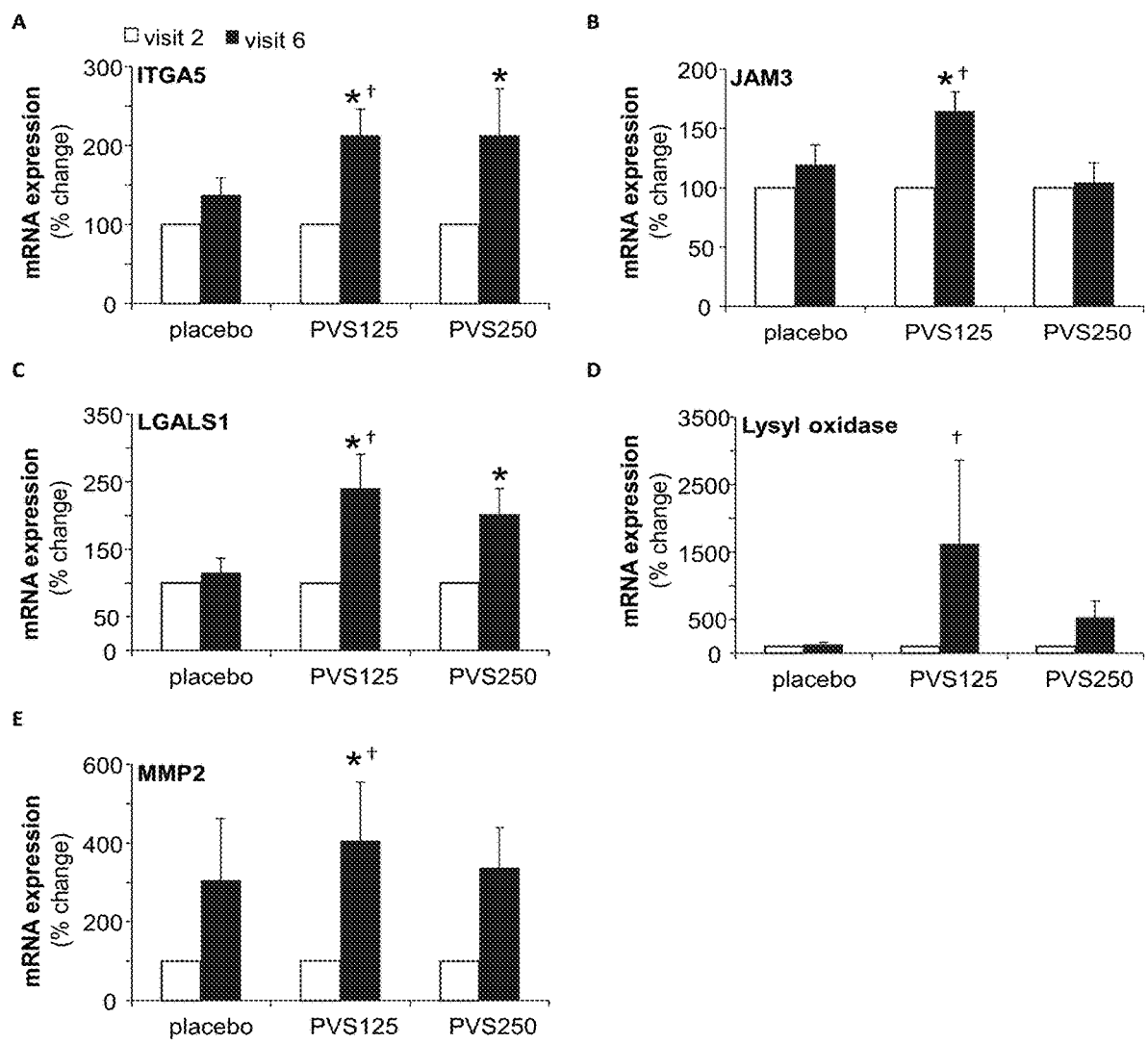
FIG. 4 depicts, in one embodiment of present invention, RTPCR validation of genes that increases movement of endothelial cells following oral PVS supplementation. Expression levels of selected genes identified by IPA were independently verified using real-time quantitative (Q) PCR. Data are mean±SEM (n=10-13); *$p<0.05$ compared to visit 2. †$p<0.05$ compared to placebo. Panels are presented as follows: A: ITGA5; B: JAM3; C: LGALS1; D: Lysyl oxidase; and E: MMP2.
Figure 5:
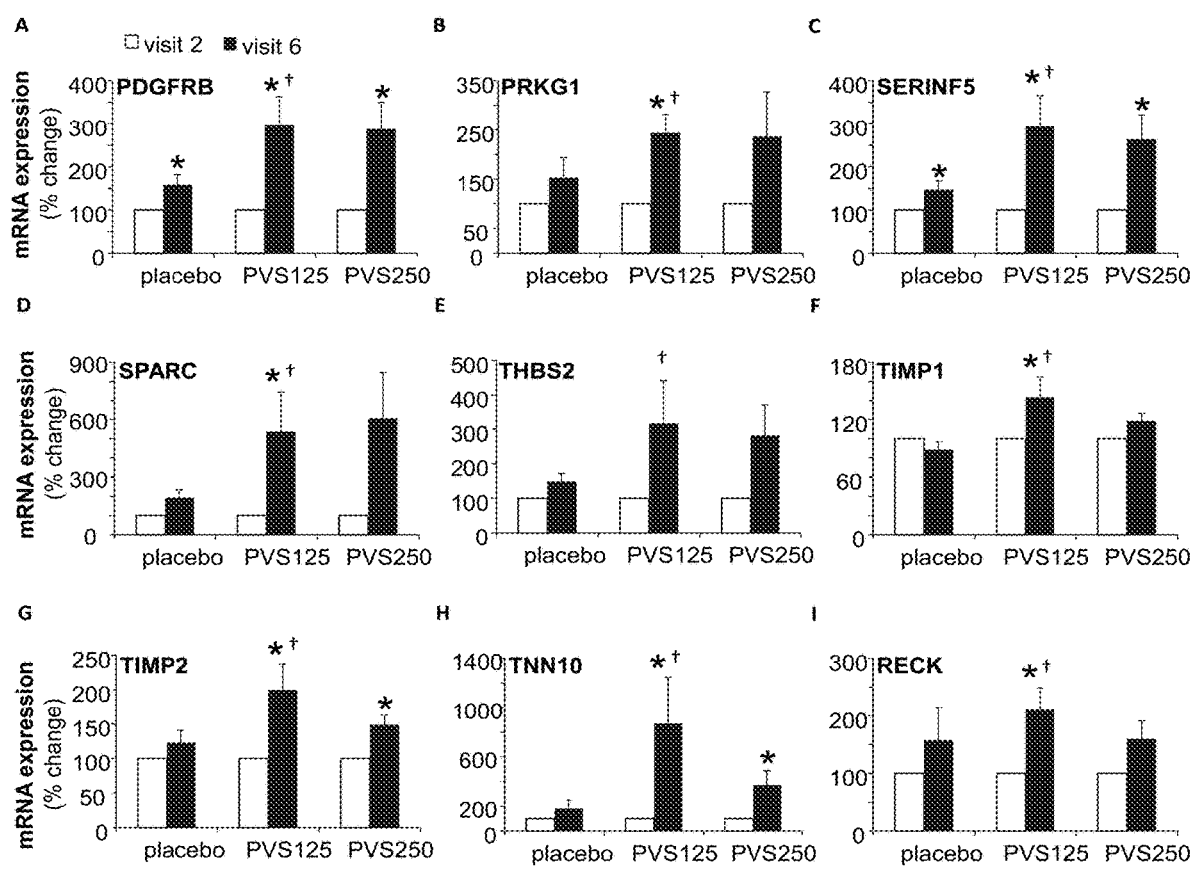
FIG. 5 depicts, in one embodiment of present invention, RTPCR validation of genes that increases growth of blood vessels following oral PVS supplementation. Expression levels of selected genes identified by IPA were independently verified using real-time quantitative (Q) PCR. Data are mean±SEM (n=10-13); *$p<0.05$ compared to visit 2. †$p<0.05$ compared to placebo. Panels are presented as follows: A: PDGFRB; B: PRKG1; C: SERINF5; D: SPARC; E: THBS2; F: TIMP1; G: TIMP2; H: TNN10; and I: RECK.
Figure 6A:
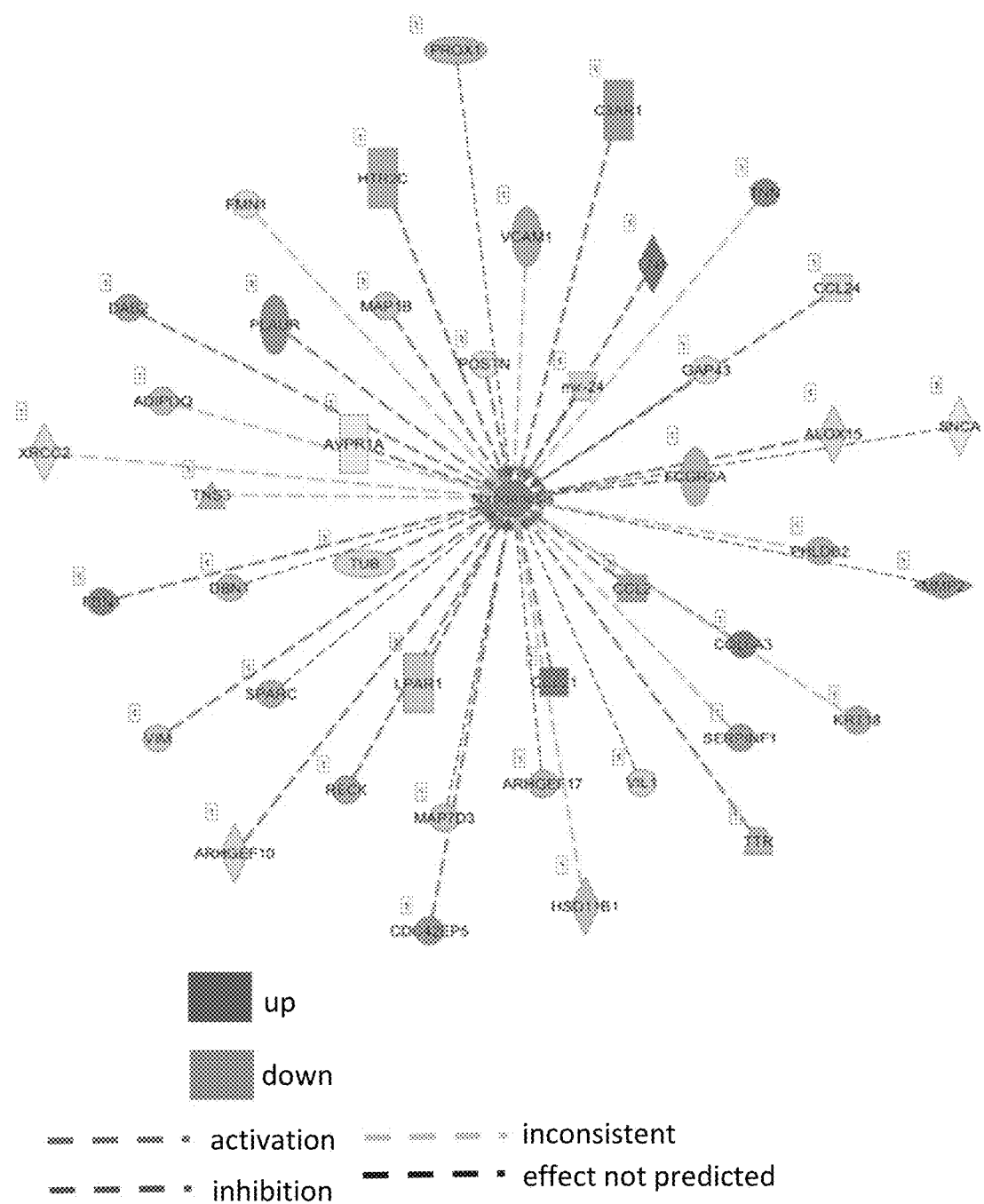
FIGS. 6A and 6B depict, in an embodiment of present invention, ingenuity pathway analysis (IPA) showing the supplementation of PVS induces ECM related genes. (Up/Down stand for up/down regulation of the genes).
Figure 6B:
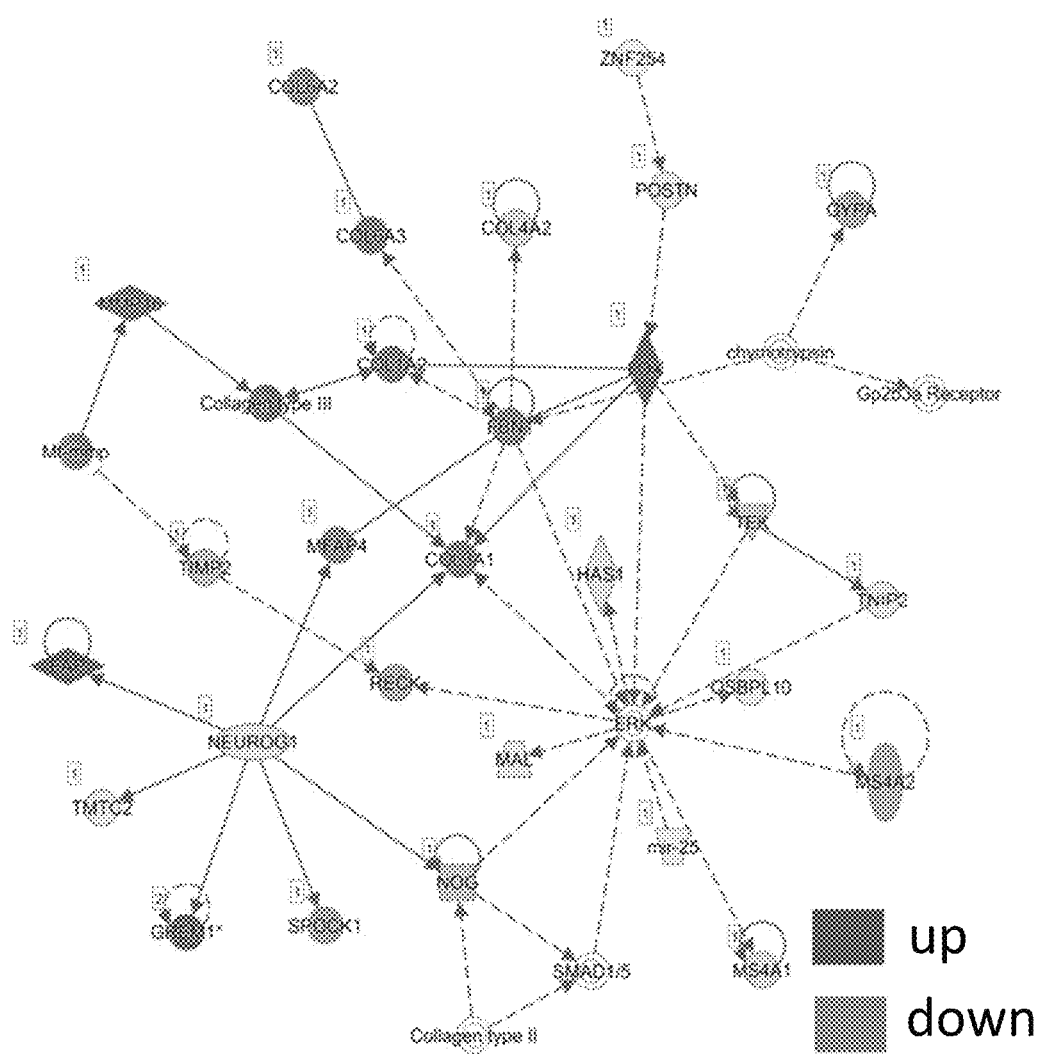
Figure 7:
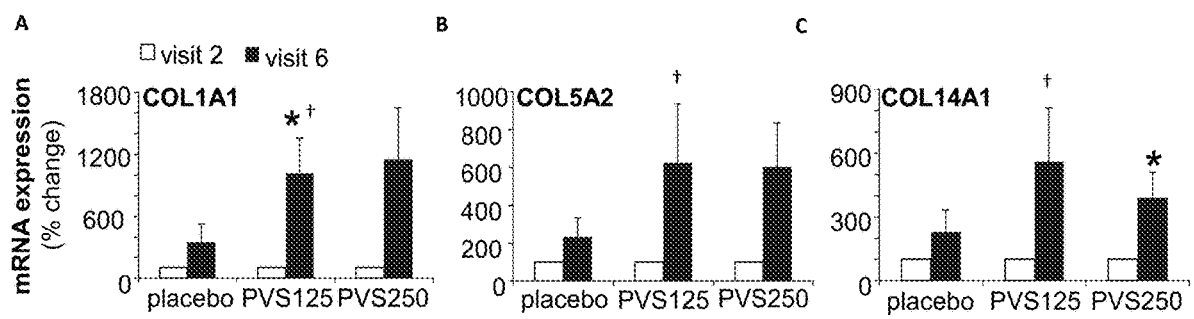
FIG. 7 depicts, in one embodiment of present invention, RTPCR validation of ECM-related genes following oral PVS supplementation. Expression levels of selected genes identified by IPA were independently verified using real-time quantitative (Q) PCR. Data are mean±SEM (n=10-13); *$p<0.05$ compared to visit 2. †$p<0.05$ compared to placebo. Panels are presented as follows: A: COL1A1; B: COL5A2; and C: COL14A1.

Ingenuity® Pathway Analysis (IPA®) is a powerful analysis and search tool that uncovers the significance of 'omics data and identifies new targets or candidate biomarkers within the context of biological systems. Pathway analysis revealed upregulated genes involved in growth of blood vessels and movement of vascular endothelial cells upon PVS supplementation (FIGS. 3A, 3B, 3C). TGFβ1 and VEGFA path of vascularization was induced by PVS supplementation (FIGS. 3A-3C). These endothelial cell migration cluster genes included: Integrin alpha-5 (ITGA5), Junctional adhesion molecule 3 (JAM3), Galectin-1 (LGALS1), Lysyl oxidase (LOX), Matrix metallopeptidase-2 (MMP2), Platelet-derived growth factor receptor beta (PDGFRB), Protein kinase, CGMP-dependent, Type 1 (PRKG1), Reversion inducing cysteine rich protein with kazal motifs (RECK), Serpin peptidase inhibitors family F (SERPINF), Secreted protein acidic and cysteine rich (SPARC), Thrombospondin 2 (THBS2), TIMP metallopeptidase inhibitor 1 (TIMP1), TIMP metallopeptidase inhibitor 2 (TIMP2), and Tenascin N (TNN). The expression of these genes was verified using quantitative real-time polymerase chain reaction (FIGS. 4 and 5) and was found to be upregulated upon PVS supplementation. In addition, an ECM related cluster of probe sets was significantly upregulated in PVS supplemented group as compared to visit 2 (FIGS. 6A, 6B). Among these up-regulated genes, Collagen type I alpha 1 (Col1A1), Collagen type V alpha 2 (Col5A2) and Collagen type XIV alpha 1 (Col14A1) were found to be significantly increased by PVS supplementation (FIG. 7).

Example 4

Safety Monitoring: PVS Supplementation Did not Adversely Affect Skin Properties

Figure 8:
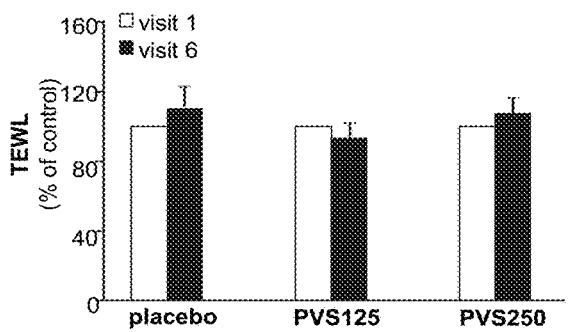
FIG. 8 depicts, in one embodiment of present invention, that PrimaVie® Shilajit is safe for facial skin. Panels are presented as follows: A, TEWL; B, Hydration; C, Elasticity; D, Viscoelasticity; and E, Retention time was measure using Dermalab Combo® as % of control. Data are mean±SEM (n=13).
Figure 8:
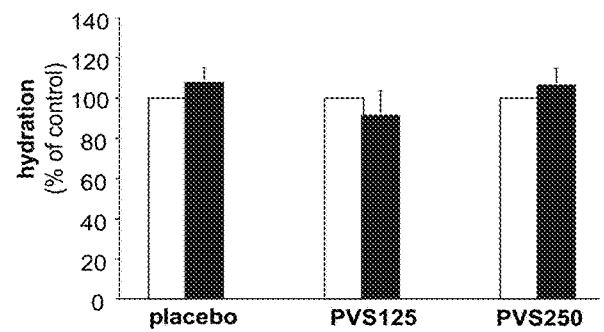
Figure 8:
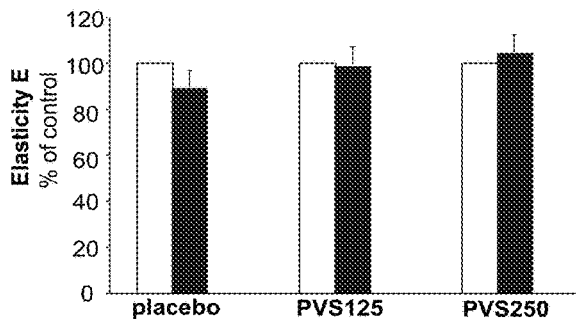
Figure 8:
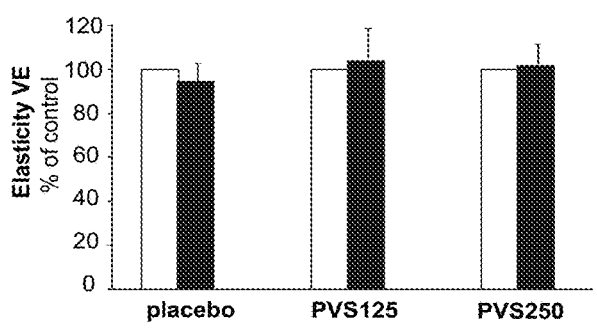
Figure 8:
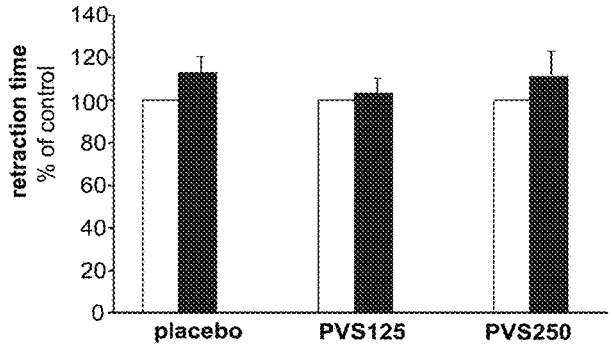

Digital macrophotography and dermascopic imaging were performed on both left and right cheeks using Dermalab Combo® device to determine the effect of PVS supplementation on the properties of the skin. Trans-epidermal water loss (TEWL), an index for skin barrier function, surface electrical capacitance for skin hydration, and skin elasticity for tissue stiffness were measured to assess the effect of PVS supplementation on skin. Analysis of trans epidermal water loss (TEWL) revealed that there is no difference in the skin integrity in the treated groups compared to the placebo (FIG. 8) indicating that the supplement intake did not affect the barrier function of the skin. Similarly, there was no significant difference in the hydration, elasticity, viscoelasticity and retraction time (FIG. 8), suggesting that PVS supplementation did not adversely affect the quality of the skin. Overall, in the clinical study Shilajit supplementation was found to be safe to the skin as it did not adversely affect the barrier function, hydration, elasticity, viscoelasticity and retraction time of the skin.

It is noted that effect of PrimaVie® Shilajit supplementation on microperfusion was statistically significant ($p \leq 0.05$) at 250 mg b.i.d. dosage when compared to the placebo, while RTPCR analysis showed that upregulation of the genes was statistically significant ($p \leq 0.05$) at 125 mg b.i.d. dosage when compared to the placebo. Such an anomaly may be attributed to the high variability in gene data and small population size in each arm of the study. The present study provided maiden evidence that oral Shilajit supplementation in adult healthy women upregulated genes related to endothelial cell migration and growth of blood vessels, likely resulting in improved skin microperfusion.

Thus, the present invention provides methods of using Shilajit, or its individual components, or a combination of two or more of these components to induce the body of a mammal, including the body of a human, to improve skin microperfusion, to upregulate ECM related genes in the skin, to increase endothelial cell migration and growth of blood vessels, and to improve skin health.

The product(s) used in the embodiments of the present invention may be formulated into nutraceutical or pharmaceutical dosage forms comprising tablets, capsules, powders, liquids, chews, gummies, transdermals, injectables, etc. using standard excipients and formulation techniques in the industry. The product(s) used in the embodiments of the present invention may be administered to the mammal orally in solid dosage form or by parenteral or transdermal administration.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%/o; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, accordingly, reference should be made to the appended claims, rather than to the foregoing specification, as indicating the scope of the invention.

What is claimed is:

1. A method of improving skin microperfusion comprising the step of administering daily for at least 14 weeks to a mammal in need of such treatment a therapeutically effective amount of Shilajit or its individual components, or a combination of two or more of these components, to improve skin microperfusion of the mammal.

2. The method of claim 1, wherein the administration of Shilajit or its individual components, or a combination of two or more of these components induces upregulation of at least one gene involved in the movement of endothelial cells, an endothelial cell migration cluster, and/or growth of blood vessels through the TGFβ1 and VEGFA pathway.

3. The method of claim 1, wherein the mammal is a human.

4. The method of claim 2, wherein the at least one upregulated endothelial cell migration cluster gene is selected from the group consisting of Integrin alpha-5 (ITGA5), Junctional adhesion molecule 3 (JAM3), Galectin-1 (LGALS1), Lysyl oxidase (LOX), Matrix metallopeptidase-2 (MMP2), Platelet-derived growth factor receptor beta (PDGFRB), Protein kinase, CGMP-dependent, Type 1 (PRKG1), Reversion inducing cysteine rich protein with kazal motifs (RECK), Serpin peptidase inhibitors family F (SERPINF), Secreted protein acidic and cysteine rich (SPARC), Thrombospondin 2 (THBS2), TIMP metallopeptidase inhibitor 1 (TIMP1), TIMP metallopeptidase inhibitor 2 (TIMP2), and Tenascin N (TNN).

5. The method of claim 1, wherein the individual components of Shilajit comprise 3-hydroxy-dibenzo-α-pyrone, 3,8-dihydroxy-dibenzo-α-pyrone, dibenzo-α-pyrone chromoproteins, humic acid, fulvic acid, and minerals.

6. The method of claim 1, wherein the mammal is a human, and wherein the dose of Shilajit is from about 20 mg to about 2,000 mg per day in humans.

7. The method of claim 1, wherein the mammal is a human, and wherein the dose of Shilajit is from about 100 mg to about 500 mg per day in humans.

8. The method of claim 2, wherein the mammal is a human, and wherein the dose of Shilajit is from about 250 mg to about 2,000 mg/day.

9. The method of claim 1, consisting essentially of said administering step.

* * * * *